United States Patent
Elsohly et al.

(10) Patent No.: US 6,365,416 B1
(45) Date of Patent: Apr. 2, 2002

(54) METHOD OF PREPARING DELTA-9-TETRAHYDROCANNABINOL

(75) Inventors: Mahmoud A. Elsohly; Samir A. Ross, both of Oxford, MS (US)

(73) Assignee: The University of Mississippi, University, MS (US)

(*) Notice: Subject to any disclaimer, the term of this patent is extended or adjusted under 35 U.S.C. 154(b) by 0 days.

(21) Appl. No.: 09/178,962

(22) Filed: Oct. 26, 1998

(51) Int. Cl.$^7$ .............................. G01N 1/40; G01N 33/15
(52) U.S. Cl. ...................... 436/177; 436/93; 436/161; 436/177; 436/178; 436/901; 514/454; 549/388
(58) Field of Search .......................... 436/93, 161, 174, 436/177, 178, 901; 210/634, 656; 203/39, 41, 73, 74, 80, 91; 514/454; 549/385, 388

(56) References Cited

PUBLICATIONS

Mechoulam et al., Fortschr. Chem. Org. NatStoffe (1967), vol. 25, pp. 175–213, 1967.*
Szepesy et al., Symp. Biol. Hung. vol. 31 (Chromatography '84), pp. 267–286, 1986.*
Wollner et al., J. Am. Chem. Soc. Vo.. 64, pp. 26–29, Jan. 1942.*

* cited by examiner

*Primary Examiner*—Jan Ludlow
(74) *Attorney, Agent, or Firm*—Eugene C. Rzucidlo; Greenberg Traurig, LLP

(57) ABSTRACT

A method of preparing THC using extraction of plant material with a non-polar solvent followed by vacuum distillation and chromatography.

11 Claims, No Drawings

METHOD OF PREPARING DELTA-9-TETRAHYDROCANNABINOL

BACKGROUND OF THE INVENTION

Delta-9-tetrahydrocannabinol (THC, also known as dronabinol) is the main biologically active component in the Cannabis plant which has been approved by the Food and Drug Administration (FDA) for the control of nausea and vomiting associated with chemotherapy and, more recently, for appetite stimulation of AIDS patients suffering from the wasting syndrome. The drug, however, shows other biological activities which lend themselves to possible therapeutic applications, such as in the treatment of glaucoma (1), migraine headaches (2,3), spasticity (4), anxiety (5), and as an analgesic (4). It is because of these-promising biological activities of THC that marijuana has been brought into a public debate relative its medicinal value. The balance between medicinal use of a drug and the abuse potential is a delicate balance. One of the main points brought by the medicinal marijuana proponents is the fact that the currently available soft gelatin capsule formulation is very expensive and lacks consistency in its effects. The latter point could be explained based on the fact that oral THC has erratic absorption from the gastrointestinal tract, is subject to the first-pass effect resulting in heavy metabolism with production of high levels of 11-OH-THC, and undesirable side effects. Another THC formulation which is currently under development is a pro-drug consisting of THC hemisuccinate formulated in a suppository base (6). This formulation appears to overcome the problems associated with the oral preparation and has been shown to produce consistent bioavailability in animal studies (7). Preliminary clinical investigations show promise for this formulation (8, 9, 10). It is anticipated that other THC formulations will be forthcoming in light of the current interest in the therapeutic activities of cannabis.

Regardless of which formulation is to be used for THC or a pro-drug thereof, a source for the raw material is critical. The currently-approved capsule formulation is prepared from synthetic THC which is extremely expensive to produce. It is thought that should an economic process be developed for isolation of THC from the natural material (cannabis), then the cost of the raw material could be brought down significantly, making it possible to develop such formulations at a reasonable cost to the public. The consequence of this would be the availability of alternative therapies involving THC (or a prodrug thereof) which would help in suppressing the public outcry for approval of marijuana as a medicine.

Several investigations have been carried out over the years to isolate THC from the plant material, mostly to determine its chemical structure or to investigate the phytochemistry of the plant. In 1942, Wollner, et al., (11) reported the isolation of tetrahydrocannabinol from cannabis extract "red oil". Red oil was prepared by extraction of the plant material with ether, followed by distillation of the concentrated extract at room pressure followed by redistillation under reduced pressure (15–50 mm Hg). The oil was acetylated with acetic anhydride, and the acetylated product was subjected to fractional distillation in vacuo. Six fractions were collected. The head and tail fractions were removed. The remaining four fractions which represented the principal fractions (fractions 2, 3, 4, and 5) were combined and passed over silica gel column in benzene and then passed over activated alumina in carbon tetrachloride solution. The product was hydrolyzed by acid, alkali, or ammonia in alcoholic solution. The authors reported that the deacetylated product has, in each case, a different physiological potency than the acetate. All fractions were not pure compounds.

DeRopp, in 1960 (12), described the isolation of THC from the flowering tops of Cannabis sativa. His method involved adsorption chromatography of the methanolic extract of cannabis followed by partition chromatography on Celite using N,N-dimethyl formamide/cychlohexane mixture and high vacuum distillation. The purity of THC was based on paper chromatographic evidence.

The first isolation of the naturally occurring THC in its pure form was reported by Gaoni and Mechoulam in 1964 (13). THC was isolated from the hexane extract of hashish by repeated column chromatography on florisil and alumina. Further purification was carried out by the preparation of the crystalline 3,5-dinitrophenylurethane of THC followed by mild basic hydrolysis to get the pure THC. The purity of THC was proven by thin layer chromatography (TLC) and spectroscopic analysis (IR and NMR).

Korte, et al., in 1965 (14) reported the isolation of THC from the crude extracts of the female inflorescence of Cannabis sativa indica and Cannabis sativa non indica. The crude extracts were chromatographed over activated alumina in order to remove the coloring impurities like carotinoids, chlorophylls, and xanthophylls. All the cannabinolic fractions were combined and concentrated to give a brownish-red oil. The oil was further purified by a countercurrent distribution method to get THC which was proved to be identical with that described by Gaoni and Mechoulam (13).

In 1967, Mechoulam and Gaoni (15) reported the isolation of THC from the acidic fraction of the hexane extract of hashish. The hexane extract of hashish was separated into acidic and neutral fractions. The acidic fraction was chromatographed on florisil or acid washed alumina. The column was eluted with pentane-ether mixtures in a manner of increasing polarities. THC was eluted with 15% ether in pentane. Repeated chromatography was carried out by the preparation of crystalline derivative (3,5-dinitrophenylurethane THC, m.p., 115–116° C.) followed by hydrolysis.

In 1972, Verwey and Witte (16) reported a method for the preparation of THC by isolation of THC acid from hashish. The hexane extract was shaken with 2% NaOH solution as well as 2% sodium sulphite in an extraction funnel. The alkaline layer was rendered acidic with $H_2SO_4$(pH<2), thus precipitating the cannabinoid acids. The oily layer as well as the oily deposits on the wall were extracted with ether. The acid-base extraction process was repeated. THC was obtained from the impure acids by heating the ether solution containing the acids on a sand bath with a temperature of 300° C. The ether being evaporated, the evaporating dish was for a moment kept on the sand bath, in this way causing decarboxylation of THC acid. The THC was cleaned by preparative TLC.

In summary, for isolation of THC and other cannabinoid constituents, generally the alcoholic or the petroleum ether or benzene or hexane extract of the plant is separated into neutral and acidic fractions. These fractions are further purified by repeated column chromatography and countercurrent distribution or a combination of these methods. Various adsorbents have been used in column chromatography, especially silica gel, silicic acid, silicic acid-silver nitrate, florisil, acid washed alumina, and acid washed alumina-silver nitrate. Most of the above-discussed methods were used for the preparation of a small amount of THC and not for large-scale production.

If THC is to be prepared in large-scale (kilogram) quantities, an efficient and economic method is needed. Such a method would require an efficient isolation procedure.

SUMMARY OF THE INVENTION

The present invention is for the preparation of THC from Cannabis plant material. Simple, high yielding steps are developed which reduce the cost of preparation of THC several fold over the synthetic route The present invention comprises a process wherein Cannabis plant material is extracted with a non-polar organic solvent to provide an extract containing THC and the extract is subjected to fractional distillation under reduced pressure to provide a distillation fraction (distillate) having a high content of THC. The instant process further comprises subjecting the extract from the plant material to column chromatography prior to fractional distillation. A still further aspect of the instant process comprises subjecting the distillate from the fractional distillation to column chromatography. Additionally, the present invention includes the use of high pressure liquid chromatography (HPLC) in the purification of the extract from the plant material.

DETAILED DESCRIPTION OF THE INVENTION

The present invention relates to a process for providing an efficient and economic method for isolating THC from Cannabis plant material. The plant material is extracted with a non-polar organic solvent. Useful solvents include lower alkanes, such as, for example, hexane, heptane or iso-octane. The extract containing THC, after solvent removal, is subjected to fractional distillation under reduced pressure and a first distillate is collected. In one embodiment of the present invention, the first distillate is again subjected to fractional distillation at reduced pressure and a second distillate is collected. The second distillate has a THC content of greater than 90% by wt.

In another embodiment of the invention the crude extract from the plant material is first subjected to column chromatography. One possible method by which the material can be placed on the column is by mixing the extract residue in an organic solvent with a portion of the column packing material and transferring the dried slurry onto the top of a packed column. Direct application of the extract residue in the initial elution solvent (minimum volume) directly to the top of the packed column is also possible. The column is eluted with an organic solvent in a manner such that the column is eluted with a solvent or a solvent mixture with progressively increasing polarity. The fraction or fractions containing the major portion of THC from the column elution is subjected to fractional distillation at reduced pressure. Distillate is collected in the substantially constant boiling temperature range and this distillate was found to contain greater than 90% by weight THC. THC with purity of greater than 95%, preferably greater than 98% can be obtained by further purification of the distillate from the fractional distillation by column chromatography or by normal or reversed phase HPLC.

The column chromatography can be carried out using any known packing material including, for example, silica or alumina for normal phase operation or $C_{18}$ or $C_8$ bonded phase silica for reversed phase operation. Elution of the normal phase chromatography column is carried out with solvents having an increasing polarity. Non-polar solvents include the lower straight chain and branched chain alkanes, including, for example, pentane, hexane, isooctane and petroleum ether. More polar solvents include various organic ethers, alcohols, esters or ketones, including, for example dialkyl ethers, lower alkyl acetates, lower dialkyl ketones and lower alkanols. Illustrative polar solvents include, for example, acetone, ethylacetate, diethylether and isopropyl alcohol. The ratio of non-polar solvent to polar solvent can vary between 100:0 to 80:20.

Elution chromatography under the reversed phase conditions is carried out with solvents having decreasing polarities. These solvents include water or acidic buffer as the polar portion and lower alkanol (such as methanol, ethanol and isopropanol) or acetonitrile as the less polar portion, in mixtures ranging from 50:50 to 0:100 aqueous to organic. The chromatographic process can also be carried out under HPLC conditions in much the same way as described above under either normal or reversed phase operation using a preparative scale column.

Flash distillation is carried out under reduced pressure, i.e. under vacuum at pressures below 1 mm Hg, preferably close to 0.1 mm Hg.

It will be understood by those skilled in the art that various modifications and substitutions may be made to the invention as described above without departing from the spirit and scope of the invention. Accordingly, it is understood that the present invention has been described by way of illustration and not limitation.

EXAMPLE NO. 1

Extraction 200 g of the air-dried and powdered buds (7.82% THC) and 270 g of the air-dried and powdered buds (6.61% THC) were mixed and extracted by maceration at room temperature with hexane for 24 hours (2.2 L Hexane×4). The hexane extracts were combined and evaporated under vacuo to give 76.5 g (16.3% extractives).

Column Chromatography 56 g of the hexane extract (40% THC) was mixed with 100 g silica gel (silica gel 60, E. Merck) and 50 ml hexane. The dried slurry was transferred onto the top of a silica gel column (850 g silica gel 60, dimensions: 10×60 cm). Elution was carried out with petroleum ether and ether in a manner of increasing polarities. Twelve fractions were collected and TLC screened. Identical fractions were pooled together. The fraction eluted with Pet.ether-ether (9:1) was evaporated to give 37.3 g of residue which showed THC content of 55.87% using gas chromatography (GC) analysis. This fraction contained the majority of THC (93%) in the material applied onto the column.

Fractional Distillation

A portion (7.1 g) of the collected fraction was subjected to fractional distillation under vacuum (between 0.08–0.1 mmHg) to get two major fractions, one collected between 170–175° C. (2.34 g @ 90% THC) and one between 175–180° C. (1.32 g @ 88.2% THC).

EXAMPLE NO. 2

Extraction

The air-dried and powdered buds (380 g, 2.20% THC) were extracted with hexane by maceration at room temperature for 24 hours (1.8 L hexane×3). The total weight of the hexane extracts was 29.1 g (7.7% extractives). The % of THC in the hexane extract was 28.76%.

Column Chromatography

The hexane extract (29.1 g) was mixed with 100 g of silica gel (silica gel 60, E. Merck) and 50 ml hexane. The dried slurry was transferred on to the top of silica gel column (850 g silica gel 60, Dimensions: 10×60 cm). Elution was carried out with petroleum ether-ether mixtures in a manner of increasing polarities. Nine fractions were collected and TLC screened. Identical fractions were pooled together to give 4 fractions. The fraction collected with petroleum ether-ether (9:1) was evaporated to yield 13.3 g of residue. GC analysis of this fraction showed a concentration of THC of 58.98%, again representing >93% recovery of all THC in the material applied to the column.

Fractional Distillation

A portion (7.3 g) of the fraction collected above was subjected to fractional distillation at vacuum (0.08–0.1. mmHg). The major fraction (3.738 g) was collected between 172–180° C. and was found to contain 89% THC by weight.

EXAMPLE NO. 3

One kg of the fine powdered marijuana plant material [average % of THC was about 5.21%] was macerated with 6 L hexanes (Hexanes GR from EM Sciences) in a percolator (9" in diameter from the top and 20" long, cone shaped) for 24 hours at room temperature and filtered. The macerate was reextracted with 5 L hexanes for another 24 hours. The hexane extracts were combined and evaporated under reduced pressure at low temperature to give 110.7 g residue (11.07% extractives). The % of THC in the hexane extract was 41.21%.

Column Chromatography

The hexane extract (110.7 g) was mixed with 150 g silica gel (silica gel 60, Art.# 9385-3) and 50 ml hexane. The air dried slurry was transferred to the top of a silica gel column (800 g silica gel 60, particle size 0.04–0.063 mm, from EM Science, Art. # 9385-3). The column was eluted with hexane: ether mixtures in a manner of increasing polarities. Fractions were collected and TLC screened (analytical silica gel plates, developing system: Hexane: Ether (80:20), Visualizing agent: Fast blue). The fractions collected with hexane (3 L.) and hexane-ether (95:5, 2 L.) were discarded. The following fractions collected with hexane-ether (95:5, 3 L.) and hexane-ether (9:1, 5 L.) were combined and evaporated to yield 77.2 g of residue. GC analysis of the residue showed THC concentration to be 54.74%.

Fractional Distillation

A portion (30.5 g) of the residue collected above was subjected to fractional distillation under reduced pressure (0.1–0.15 mm/Hg). The temperature was slowly raised to 125° C. and the materials collected were kept separate. The temperature was then raised between 140–160° C. where the major fraction was collected (14 g). GC analysis showed >96% THC.

EXAMPLE NO. 4

One kg of the fine powdered marijuana plant material [average % of THC is 4.42] was macerated with 6 L hexanes and extracted by the same procedure followed in Example 3 to yield 105.8 g residue (10.58% extractives). The % of THC in the hexane extract was 40.35% by GC analysis.

Direct Fractional Distillation of the Hexane Extract

A portion (23.0 g) of the hexane extract was subjected to fractional distillation under reduced pressure (vacuum, 0.1–0.2 mm/Hg). The temperature was raised slowly to 160° C. where a small amount of material (<1 g) was collected and left separate. The major fraction (10.1 g) was collected between 170 and 180° C. GC analysis of this fraction showed 72.66% THC concentration.

A second portion (25.0 g) of the hexane extract was subjected to fractional distillation under similar conditions as the first portion. The major fraction collected between 170–180° C. weighed 11.6 g and had a THC concentration of 73.62%.

A third portion (25.0 g) of the hexane extract was subjected to fractional distillation under similar conditions to the previous portions. The major fraction containing THC weighed 10.2 g and had a THC concentration of 73.72%.

The three major fractions obtained from the above three distillations were combined and analyzed. The analysis showed the concentration of THC to be 70.31%. The mixture (28.9 g) was subjected to fractional distillation, again under similar conditions. The temperature was raised slowly to 135° C. under vacuum (0.1–0.15 mmHg) and the fractions collected were kept aside. The major THC containing fraction was collected at 140–160° C. and 0.05–0.06 mm/Hg. The fraction weight was 18.4 g and the THC content was 92.15%.

EXAMPLE NO. 5

A portion (0.8 g) of the pure THC obtained in Example No. 3 (% of THC was about 96%) was mixed with one gram silica gel (silica gel 60) and one ml hexane. The dried slurry was transferred on to the top of a silica gel column (12 silica gel 60, Dimensions: 1×50 cm). Elution was carried out with hexane:ether mixtures in a manner of increasing polarities. Six fractions were collected and screened using TLC. Fraction Nos. 3–5 (hexane:ether 98:2) were combined and yielded 0.63 g of residue (% of THC was 98%).

EXAMPLE NO. 6

One gram of the THC prepared in Example No. 4 (purity was about 92%) was mixed with one gram of silica gel (silica gel 60) and one ml hexane. The dried slurry was transferred on to the top of a silica gel column (13 g silica gel 60, dimensions: 1×50 cm). Elution was carried out under similar conditions as under Example 5. Fraction nos. 3–5 yielded 0.78 g of residue (% of THC was 98%).

EXAMPLE NO. 7

1000 g of the air-dried and powdered Cannabis buds % of THC by GLC analysis was 6.49%) were extracted by maceration at room temperature for 24 hours (5 L×3, Lot. No. 970424). The hexane extracts were combined and evaporated under vacuo to give 97 g residue.

67 g of the hexane extract was dissolved in 200 ml isooctane (Lot. No. 904038) and the solution was transferred onto the top of a silica gel column (280 g silica gel, 40 $\mu$m particle size, dimensions of column: 10×60 cm). The column was eluted with iso-octane:methyl-t-butyl ether mixture 8:2 (3 L, fraction 1) and then washed with methanol (1 L, fraction 2). GLC analysis of fraction 1 (53 g) showed a concentration of THC of 55.56%.

Fractional Distillation

Fraction 1 (53 g) was subjected to fractional distillation at vacuum 0.1–0.6 mm/Hg. The major fraction (20.0 g) was collected between 160–170° C. and was found to contain 94% THC by weight.

Purification of THC by HPLC 10 g of the major fraction (purity about 94%) was purified on HPLC (water Delta prep 4000) connected to a Waters 486 Tunable absorbance detector and using column Prep PAK500/silica. The eluent was iso-octane:methyl-t-butyl ether mixture (98:2). The flow rate was programmed to be 10 ml/minute for 10 minutes, 25 ml/minute for 60 minutes and finally 50 ml/minute for 200 minutes.

The results are summarized in the following table:

| FRACTIONS | TIME (minutes) | VOLUME (ML) | WEIGHT (G) | ANALYSIS FOR THC |
|---|---|---|---|---|
| 1 | 22–48 | 600 | trace | |
| 2 | 67–72 | 300 | 0.3 g | |
| 3 | 72–74 | 100 | 0.9 g | |
| 4 | 74–81 | 450 | 2.7 g | 96.6% |
| 5 | 81–97 | 800 | 4.0 g | 99.0% |
| 6 | 97–100 | 1200 | 1.9 g | 97.5% |

Purification of THC Prepared by Fractional Distillation Using Flash Column Chromatography

EXAMPLE NO 8

2.1 g of THC (91% purity) were dissolved in 10 ml isooctane and the solution was transferred onto the top of a silica gel column (30 g silica gel, 40 μm particle size; dimensions of the column: 2.5 cm×40 cm). The column was eluted with isooctane then a mixture of isooctane-acetone (99:1). Seven fractions were collected and analyzed by GLC. Isooctane-acetone (99:1) fractions containing the bulk of the THC were contained and yielded 1.84 g of residue (% of THC was 97%).

EXAMPLE NO. 9

1 g of THC (91% purity) was dissolved in 5 ml isooctane and the solution was transferred onto the top of a silica gel column (15 g silica gel, 40 μm particle size, dimensions: 2.5 cm×40 cm). The column was eluted with isooctane-ethyl acetate mixture in a manner of increasing polarities and the fractions were collated. Fraction No. 5 (eluted with isooctane-ethylaetate 98:2) yielded 0.56 g of residue (% of THC was 97%). Fraction No. 4 (eluted with iso-octane-ethylacetate 98.5:1.5) yield 0.32 g of residue (% of THC was 94.9%).

EXAMPLE NO. 10

1.1 g of THC (91% purity) was dissolved in 5 ml isooctane and the solution was transferred onto the top of a silica gel column (15 g silica gel, 40 μm particle size, dimensions: 2.5 cm×40 cm). The column was eluted with a mixture of isooctane: isopropyl alcohol in a manner of increasing polarities. Five fractions were collected. Fraction Nos. 4 and 5 (eluted with iso-octane-isopropyl alcohol (98:2 and 95:5, respectively) were combined and yielded 1g of residue (% of THC was 94%).

Purification of THC by HPLC (Reversed Phase)

EXAMPLE NO. 11

9.6 g of THC (purity 92.8%) was purified on HPLC (Water Delta Prep 4000) connected to Waters 486 Tunable absorbance detector (wave length used: 254 nm) and using Column Prep Pak C18 (from Waters, Dimensions 46 mm×30 cm, 55–105, μm, Lot no. T 72852). The eluent was a mixture of methanol: water (75:25). The flow rate was programmed to be 10 ml/minute for 10 minutes, 25 ml/minute for 50 minutes and finally 50 ml/minute for 140 minutes. The results are summarized in the following table:

| Fraction | Time (minutes) | Volume (ml) | Weight (g) | Analysis for THC |
|---|---|---|---|---|
| 1 | 69–96 | 1400 | 0.10 | |
| 2 | 96–105 | 500 | 0.34 | |
| 3 | 105–123 | 1000 | 6.00 | 99% |
| 4 | 123–135 | 600 | 1.98 | 98% |
| 5 | 135–155 | 1000 | 1.00 | 95% |
| 6 | 174–180 | 300 | 0.10 | |

SUMMARY

1. THC can be prepared directly from a hexane extract of *Cannabis sativa L.* by double fractional distillation. The purity of THC by GLC analysis is about 90–92%. Further purification on a silica gel column gives THC with approximately 98% purity.
2. THC can be prepared directly from a hexane extract of *Cannabis sativa L.* by column chromatography (silica gel) followed fractional distillation. The purity of THC is about 95–96%. Further purification on a silica gel column gives THC with at least 98% purity.

REFERENCES

1. ElSohly, M. A.; Harland, E.; and Waller, C. W.; Cannabinoids in glaucoma II: The effect of different cannabinoids on the intraocular pressure of the rabbit; *Curr. Eye Res.;* 3(6):841–850, 1984.
2. El-Mallakh, R. S.; Marihuana and migraine, *Headache,* 27(3):442–443, 1987.
3. Volfe, Z.; Dvilansky, I. A., and Nathan, I.; Cannabinoids block release of serotonin from platelets induced by plasma from migraine patients; *Int. J. Clin Pharmacol. Res.,* 5(4):243–246, 1985.
4. Maurer, M; Henn, V.; Dirtrich, A.; and Hofmann, A.; Delta-9-tetrahydrocannabinol shows antispastic and analgesic effects in a single case double-blind trial; *Eur. Arch. Psychiatry Clin. Neurosci.,* 240(1):1–4, 1990.
5. McLendon, D. M., Harris, R. T.; Maule, W. F.; Suppression of the cardiac conditioned response by delta-9-tetrahydrocannabinol: A comparison with other drugs; *Psychopharmacology,* 50(2): 159–163, 1976.
6. ElSohly, M. A., Stanford, D. F.; Harland, E. C.; Hikal, A. H.; Walker, L. A.; Little, T. L., Jr.; Rider, J. N.; and Jones, A. B.; Rectal bioavailability of delta-9-tetrahydrocannabinol from the hemisuccinate ester in monkeys; *J. Pharm. Sci.,* 80(10):942–945, 1991.
7. ElSohly, M. A., Little, T. L., Jr.; Hikal, A.; Harland, E.; Stanford, D. F.; and Walker L. A.; Rectal bioavailability of delta-9-tetrahydrocannabinol from various esters; *Pharmacol., Biochem., Behav.,* 40:497–502, 1991.
8. Mattes, R. D.; Shaw, L. M.; Edling-Owens, J., Engleman, K.; and ElSohly, M. A.; Bypassing the first-pass effect for the therapeutic use of cannabinoids; *Pharm., Biochem., Behav.,* 44(3):745–747, 1991.
9. Mattes, R. D.; Engelman, K.; Shaw, L. M.; and ElSohly, M. A.; Bypassing the first-pass effect for the therapeutic use of cannabinoids, *Pharmacol., Biochem., Behav,* 49(1):187–195, 1994.
10. Brenneisen, R.; Egli, A.; ElSohly, M. A.; Henn, V.; and Speiss, Y.; The effect of orally and rectally administered delta-9-tetrahydrocannabinol on spasticity: A pilot study with 2 patients; *Inter. J. Clin. Pharmacol. and Therapeutics,* 34(10):446–452, 1996.
11. Wollner, H. J.; Matchett, J. R.; Levine, J.; and Loewe, S.; Isolation of a physiologically active tetrahydrocannabinol from *Cannabis sativa* resin; *J. Am. Chem. Soc.,* 64:26–29, 1942.

12. DeRopp, R. S.; Chromatographic separation of the phenolic compounds of *Cannabis sativa; J. Am. Pharmacol. Assoc., Sci. Ed.,* 49:756, 1960.
13. Gaoni, Y.; and Mechoulam, R.; Isolation, structure, and partial synthesis of an active constituent of hashish; *J. Am. Chem. Soc.,* 86:1646–1647, 1964
14. Korte, F.; Sieper, H.; and Tira, S.; New results on hashish-specific constituents; *Bull. Narcotics,* 17:35–43, 1965.
15. Mechoulam, R.; and Gaoni, Y.; Recent advances in chemistry of hashish; *Fortschr. Chem. Org. NatStoffe,* 25:175–213, 1967.
16. Verwey, A. M. A.; and Witte, A. H.; A rapid method of preparation of THC by isolation of THCA from hashish; *Pharm. Weekblad,* 107:415–416, 1972.

What is claimed is:

1. A method for the isolation of delta-9-tetrahydrocannabinol (THC) from cannabis plant material in large-scale quantities comprising:
    a) extracting the Cannabis plant material with a non-polar organic solvent to form an extract;
    b) removing the solvent from the extract to give an extract residue;
    c) optionally, subjecting the extract residue to column chromatography to give a residue eluate;
    d) subjecting one of the extract residue or the residue eluate provided by column chromatography to a first low pressure flash distillation and collecting a first distillate containing THC from a constant boiling range in the distillation;
    e) optionally, subjecting the first distillate to a second low pressure flash distillation to give a second distillate containing THC; and
    f) subjecting one of the first distillate obtained from the first flash distillation or the second distillate obtained from the second flash distillation to at least one of column chromatography, normal HPLC, or reversed HPLC to provide a product containing delta-9-tetrahydrocannabinol.

2. The method of claim 1, further comprising subjecting the first distillate obtained from the first flash distillation or the second distillate obtained from the second flash distillation to column chromatography using solvents or solvent mixtures having progressively increasing polarities and collecting an eluate containing THC.

3. The method of claim 1, further comprising subjecting the extract residue to column chromatography by elution with solvents or solvent mixtures having progressively increasing polarities and collecting fractions containing THC prior to the first flash distillation.

4. The method of claim 3, further comprising subjecting the first distillate obtained from the first flash distillation or the second distillate obtained from the second flash distillation to column chromatography by elution with solvents or solvent mixtures with progressively increasing polarities and collecting fractions containing THC therefrom.

5. The method of claim 3, further comprising subjecting the first distillate obtained from the first flash distillation or the second distillate obtained from the second flash distillation to normal phase HPLC using solvents or solvent mixtures with progressively increasing polarities and collecting fractions containing THC therefrom.

6. The method of claim 3, further comprising subjecting the first distillate obtained from the first flash distillation or the second distillate obtained from the second flash distillation to reversed phase HPLC using solvents or solvent mixtures with progressively decreasing polarities and collecting fractions containing THC therefrom.

7. The method of claim 1, further comprising subjecting the first distillate obtained from the first flash distillation or the second distillate obtained from the second flash distillation to normal phase HPLC using solvents or solvent mixtures with progressively increasing polarities and collecting fractions containing THC therefrom.

8. The method of claim 1, further comprising subjecting the first distillate obtained from the first flash distillation or the second distillate obtained from the second flash distillation to reverse phase HPLC using solvents or solvent mixtures with progressively decreasing polarities and collecting fractions containing THC therefrom.

9. The method of claim 1, further comprising collecting a distillate containing THC in an amount greater than 90 percent by weight.

10. A method for the isolation of delta-9-tetrahydrocannabinol (THC) from cannabis plant material in large-scale quantities comprising:
    a) extracting the Cannabis plant material with a non-polar organic solvent to form an extract;
    b) removing the solvent from the extract to give an extract residue;
    c) subjecting the extract residue to column chromatography to give a residue eluate;
    d) subjecting the residue eluate provided by column chromatography to a first low pressure flash distillation and collecting a first distillate containing THC from a constant boiling range in the distillation;
    e) optionally, subjecting the first distillate to a second low pressure flash distillation to give a second distillate containing THC; and
    f) subjecting one of the first distillate obtained from the first flash distillation or the second distillate obtained from the second flash distillation to at least one of column chromatography, normal HPLC, or reversed HPLC to provide a product containing delta-9-tetrahydrocannabinol.

11. A method for the isolation of delta-9-tetrahydrocannabinol (THC) from cannabis plant material in large-scale quantities comprising:
    a) extracting the Cannabis plant material with a non-polar organic solvent to form an extract;
    b) removing the solvent from the extract to give an extract residue;
    c) subjecting the extract residue to column chromatography to give a residue eluate;
    d) subjecting the residue eluate provided by column chromatography to a first low pressure flash distillation and collecting a first distillate containing THC from a constant boiling range in the distillation;
    e) subjecting the first distillate to a second low pressure flash distillation to give a second distillate containing THC; and
    f) subjecting the second distillate obtained from the second flash distillation to at least one of column chromatography, normal HPLC, or reversed HPLC to provide a product containing delta-9-tetrahydrocannabinol.

* * * * *